United States Patent [19]

Harris

[11] 4,198,991

[45] Apr. 22, 1980

[54] CARDIAC PACER LEAD

[75] Inventor: Donald L. Harris, Miami Beach, Fla.

[73] Assignee: Cordis Corporation, Miami, Fla.

[21] Appl. No.: 906,981

[22] Filed: May 17, 1978

[51] Int. Cl.² .............................................. A61N 1/04
[52] U.S. Cl. .................................. 128/784; 128/419 P
[58] Field of Search ................... 128/404, 418, 419 P, 128/783, 784, 786

[56] References Cited

U.S. PATENT DOCUMENTS

| | | | |
|---|---|---|---|
| 3,367,339 | 2/1968 | Sessions | 128/418 |
| 3,490,442 | 1/1970 | Strev | 128/418 |
| 3,568,660 | 3/1971 | Ctrites et al. | 128/419 P |
| 3,731,376 | 5/1973 | Ackerman | 128/418 |
| 3,924,639 | 12/1975 | Hess | 128/418 |
| 4,030,508 | 6/1977 | Thalen | 128/418 |

FOREIGN PATENT DOCUMENTS 1219017 1/1971 United Kingdom ................. 128/419 P

*Primary Examiner*—William E. Kamm
*Attorney, Agent, or Firm*—Kenway & Jenney

[57] ABSTRACT

In the cardiac pacer lead construction disclosed herein, long life and fatigue resistance is obtained by utilizing as a conductive element a thread of conductive carbon filaments in a resin matrix. The thread is helically wound between a stimulation electrode structure at the distal end of the lead and a terminal at the proximal end, the terminal being adapted for connection to a stimulation pulse generating circuit.

8 Claims, 9 Drawing Figures

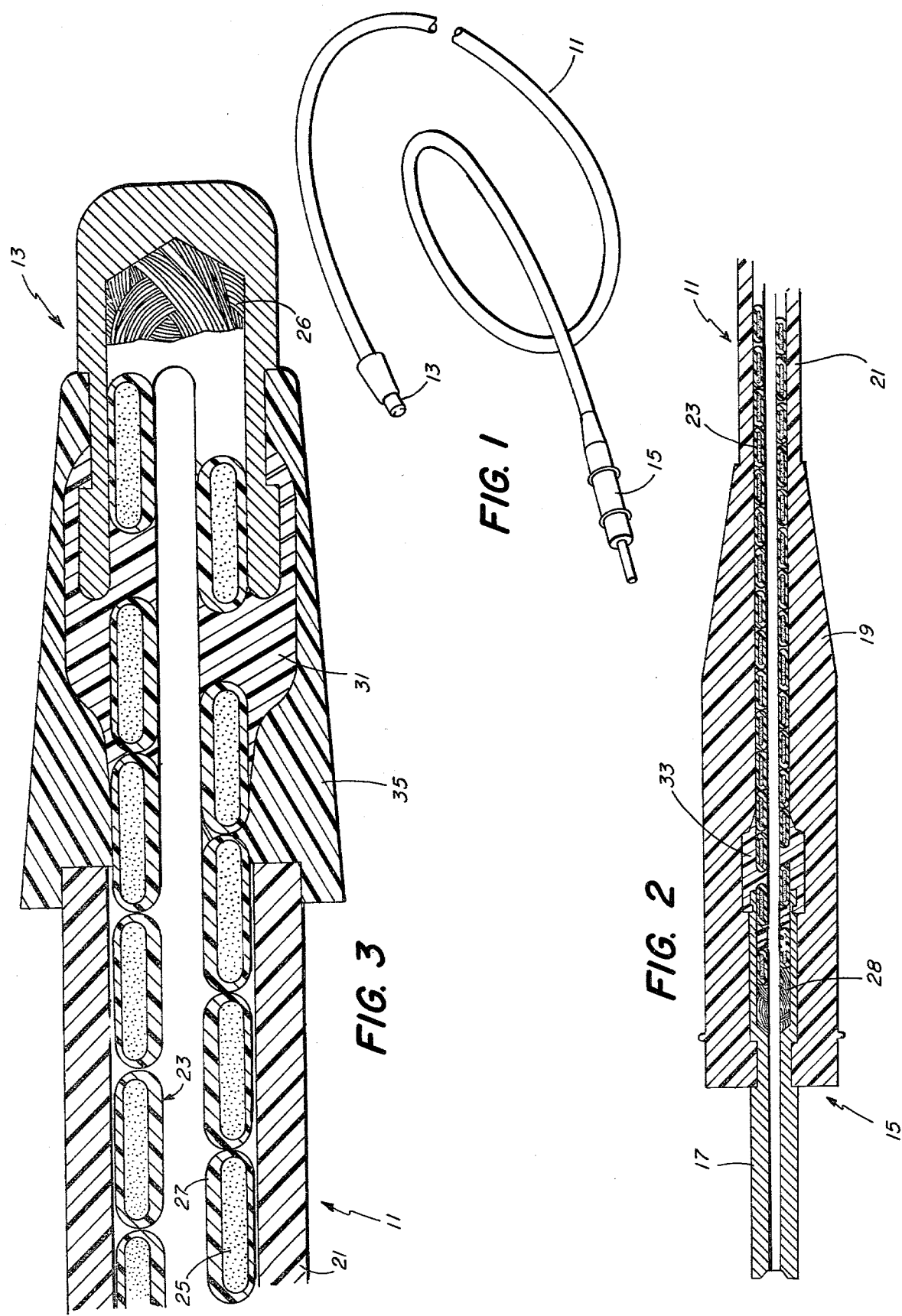

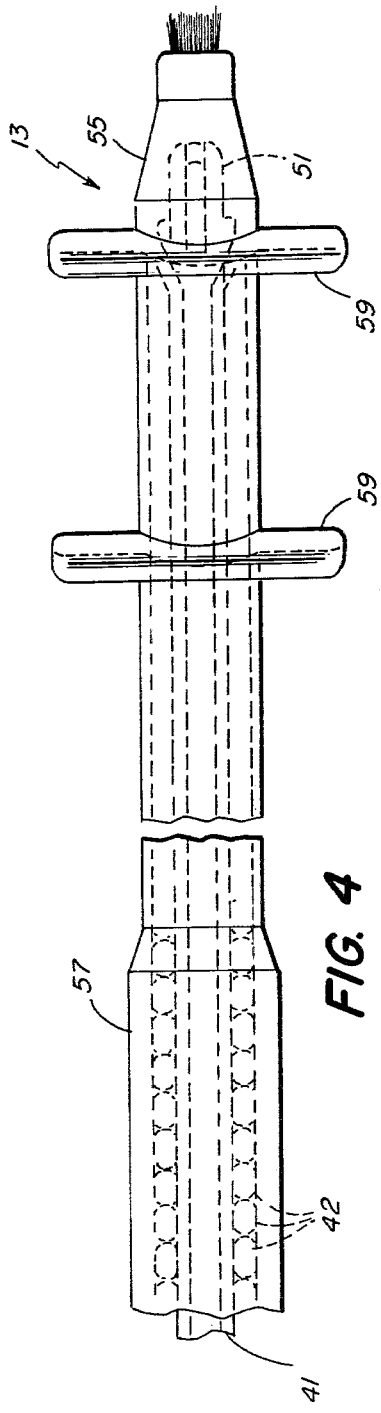
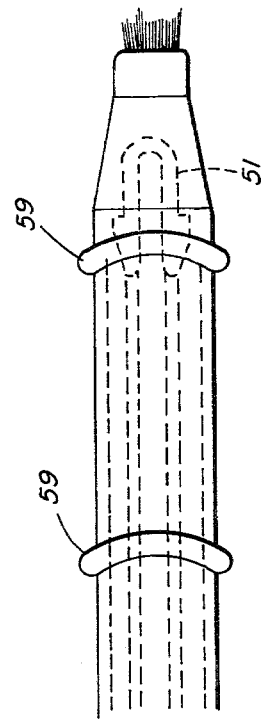
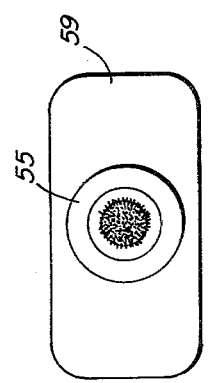
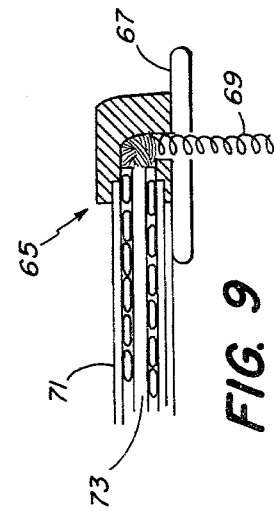
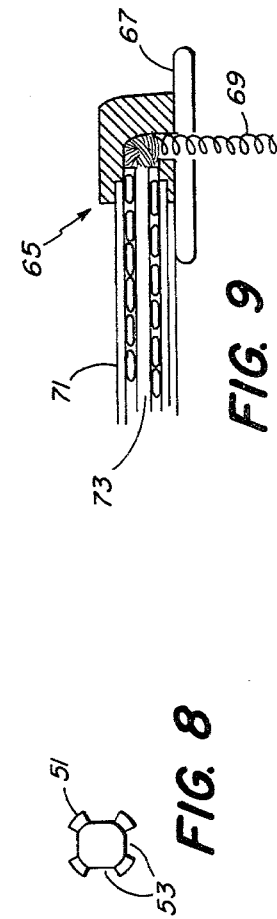

CARDIAC PACER LEAD

BACKGROUND OF THE INVENTION

The present invention relates to leads for cardiac pacing and more particularly to such a lead having high fatigue resistance and tolerance for physical abuse.

Cardiac pacing by means of an implantable electronic stimulator has come into increasing acceptance for treatment of a variety of cardiac ailments and arrhythmias. Various types of pacing systems are presently available which may stimulate the patient's ventricle, atrium, or both. Various pacing modes are employed, including those commonly known as fixed rate, standby, and synchronous pacing. Except for the seldom used fixed rate mode, most of these forms of pacing are responsive to electrical signals occurring spontaneously at the heart as a result of natural cardiac activity.

In virtually all popular pacing systems, the electronic pulse generator circuit, together with its associated batteries, is positioned at a site somewhat remote from the heart itself and electrical connections to the heart are made by means of flexible leads. In the case of epicardial lead placement, i.e., where the electrode is placed on the exterior of the heart, the electronic pacer itself is typically located in the abdominal cavity. In endocardial pacing, the pacemaker circuit is often located in the subcutaneous pocket near the patient's shoulder and a lead is introduced into the patient's heart through a vein. In each case, the lead is subject to continuous flexing due to the beating of the heart and to the patient's other natural movements, including breathing. Accordingly, substantial efforts have been directed at developing leads which ade resonably pliant and highly fatigue resistant. Despite such efforts, however, lead failure remains a significant problem with pacing system longevity, increasingly so as longer-lived and more reliable battery systems are developed.

One of the more popular types of lead is one in which the body of the lead, i.e., the portion extending between the stimulation electrode and the pacer connection, comprises a helical coil of Elgiloy wire fitting loosely within an insulating tube or sheath of silicone rubber. Elgiloy is an alloy developed for its high fatigue resistance and the helical winding arrangement minimizes stress concentrations under most circumstances. Such a lead is relatively compliant and long-lived, but longer life still is desired. In installing an endocardial lead of this general construction, the lead is typically stiffened during installation by the insertion of a stylet which passes through the center of the helix, the connector at the proximal end of the pacer lead being tubular for admitting the stylet. The stylet stiffens the lead so that it can be threaded through the vein into the patient's heart and appropriately positioned within the patient's heart. The stylet is then removed before the lead is connected to the stimulation pulse generator circuit. This method of lead introduction is a desirable feature of any endocardial lead. Even with this configuration, however, life expectancy of the lead is not unlimited, and replacement may ultimately be required.

Among the several objects of the present invention may be noted the provision of a lead for cardiac pacing which provides exceptionally long life and fatigue resistance; the provision of such a lead which is highly reliable and which is resistant to physical abuse; the provision of such a lead which is easy to introduce; the provision of such a lead providing desirable electrical conduction properties; the provision of such a lead which is relatively well-tolerated by the patient's body upon implantation; the provision of such a lead which facilitates contact with cardiac tissue; and the provision of such a lead which is of simple and relatively inexpensive construction. Other objects and features will be in part apparent and in part pointed out hereinafter.

SUMMARY OF THE INVENTION

Briefly, a cardiac pacing lead in accordance with the present invention employs, as its flexible conductive element, one or more threads of conductive carbon filaments in a resin matrix, the thread typically extending between a stimulation electrode structure at the distal end of the lead and a terminal at the proximal end of the lead, the terminal being adapted for connection to a cardiac stimulation pulse generator circuit. A flexible insulating sheath extends over the thread from the electrode to the terminal.

Carbon in a high modulus graphite filament form is availble from several commercial sources, including Union Carbide Corporation, which sells such materials under its trademark Thornel. The principal use for these fibers is as resin reinforcement replacing fiberglass for very high strength and high temperature application. Some forms of these fibers are fairly conductive, although this property has by and large been utilized only to facilitate electrostatic spray painting of parts in accordance with typical automotive practice.

BRIEF DESCRIPTION OF THE DRAWINGS

FIG. 1 is an overall view of a cardiac pacer lead constructed in accordance with the present invention;

FIG. 2 is a cross-sectional view, in enlarged scale, illustrating the construction of a connector employed in the FIG. 1 lead and its connection to the flexible body of that lead;

FIG. 3 is a cross-sectional view, to further enlarged scale, showing the stimulation electrode tip and further detailing the construction of the flexible body portion of the lead;

FIG. 4 is a plan view of an alternative embodiment in the lead of the present invention;

FIG. 5 is a side view of the tip portion of the lead of FIG. 4;

FIG. 6 is an end-on view of that tip;

FIGS. 7 and 8 are detailed views of a stylet stop employed in the electrode of FIG. 4; and FIG. 9 is a side view, with portions broken away, of an epicardial lead constructed in accordance with the present invention.

Corresponding reference characters indicate corresponding parts throughout the several views of the drawings.

DESCRIPTION OF THE PREFERRED EMBODIMENTS

Referring now to FIG. 1, the cardiac pacing lead illustrated there comprises an elongate flexible body portion 11 having at its distal end a metallic electrode tip portion 13 adapted for contacting cardiac tissue and having at its proximal end a connector 15 adapted for connection to a pulse generating circuit. The connector 15 is essentially conventional, including a generally tubular metal terminal portion 17 (FIG. 2) and a shaped silicone rubber jacket 19 facilitating a sealed electrical connection with the stimulation pulse generating circutry. The terminal 17 is centrally apertured as indicated so that a stylet can be introduced into the lead so as to stiffen it during installation.

The lead body 11 includes a flexible tubular body cover 21 such as silicone rubber which is fitted loosely over a helically wound conducting element 23 and bonded to the terminal jacket 19 and the tip jacket 35. As shown in greater detail in FIG. 3, the conducting element 23 has a generally flat ribbon-like cross-sectional configuration and includes a conductive core portion 25 of parallel cabon filaments in a resin matrix together with a resinous sheath 27. A suitable form of conductive carbon filament material is available from Union Carbide Corporation, Carbon Products Division, under its product designation "THORNEL" 300, WYP 15 I/O. This material is available from the manufacturer with a 10% Teflon (tetrafluoroethylene) impregnation.

The conductive element 23 is formed by flattening the impregnated thread material obtained from the manufacturer and then extruding, over the thread, the Teflon sheath 27 in a cross-head extruder of conventional construction. A second method is to extrude the Teflon sheath separately and pull the thread through later. The material is then wound on a mandrel to obtain the desired helical configuration and is then heated to set the material in that shape, the heating procedure being chosen in relation to the particular resin materials employed. The helically coiled conductive element can then be inserted through the silicone rubber tube 21.

To establish the electrical connection at each end of the conductive element, the carbon filaments themselves are first bared and are then bonded with a conductive, e.g., silver-or platinum-loaded, epoxy adhesive to the metal electrode and terminal components, i.e. as indicated at 26 and 28 respectively. The individual carbon filaments may be bared by heating since the carbon will withstand much higher temperatures than the resin matrix. The bared filaments are preferably then washed in a solvent to remove any residue left by the resins upon decomposition.

A relatively hard resin, such as methylmethacrylate, is preferably molded around the last turn or so of the conductive element adjacent each of the connections, as indicated at 31 and 33, to act as a strain relief and as a moisture barrier for the epoxy. The jacket 19 is then molded around the terminal 17, extending to and bonded with the tube 21 which surrounds the conductive element 23. Similarly, a conically shaped jacket 35 of silicone rubber is molded at the electrode end of the lead body, joining the tube 21 to the stimulation electrode tip 13.

As compared with the winding of Elgiloy wire in conventional leads, the winding of the carbon filament conductive element is preferably done at a relatively wide draft angle so that a wide strand or multiple strands can be used, and so that the length of each thread is relatively short as compared with the total length of wire normally required to make up a conventional Elgiloy lead. For comparison, it may be noted that a standard Elgiloy lead 62 cm. long uses 555 cm. of Elgiloy wire, whereas a lead of the same length constructed in the manner illustrated employs a carbon filament strand of 130 cm. in length. The greater flexibility and fatigue resistance of the carbon filament material allows this broader winding angle and yet still yields much higher fatigue resistance. The broader winding angle in turn allows a broader or multiple parallel threads to be used, which are individually of shorter length, and further are electrically in parallel. Thus, though carbon filaments are relatively poor conductors as compared with metal and accordingly do not suggest themselves as wire substitutes, in fact a lower total resistance can be obtained from terminal to tip using the construction illustrated as compared with the comparable Elgiloy wire construction. For example, a conventional Elgiloy lead of 61 cm. length will exhibit a resistance of 89 ohms, whereas a lead of the same length constructed as described above with one carbon thread will exhibit a resistance of about 128 ohms and with two carbon threads about 43 ohms, owing to the broader winding angle. Where elastic elongation of the overall lead is not deemed necessary, it is possible, with the carbon material, to have the conductive element extend fully parallel to the lead axis producing an even lower resistance.

While a conventional electrode may be used for contacting the cardiac tissue, as described above, a presently preferred form of terminating an endocardial lead according to the present invention is to carry the carbon filaments themselves through the electrode structure and to have them project from the lead tip in a brush-like electrode structure. An alternative embodiment employing this construction is illustrated in FIGS. 4–7.

A plurality of carbon filament strands 42 are bonded to a pulse generator connector (not shown), e.g. by means of conductive adhesive, and are then wound helically around a core tube 41. In a preferred construction of this form of lead, four such strands or threads were used, each thread being itself of about 0.4 mm diameter and comprising approximately 3000 individual carbon filaments, each filament being on the order of 7 microns diameter. The filaments comprising each strand are thoroughly impregnated with a resin matrix which prevents the individual filaments from breaking and destructing each other as the lead flexes and which bonds the filaments into a cohesive mass. A suitable resin matrix is Teflon such as the type emulsion 30-B manufactured by the DuPont de Nemours, E.I. & Co. of Wilmington, Del. A particularly thorough impregnation of the filaments may be obtained by submersing the strand in a 10% Teflon emulsion dispersed in 1% polyurethane binder followed by heat treatment. Other means of working the resin into the fibers may also be satisfactorily employed.

The tip portion of this lead includes a highly radiopaque tungsten stylet stop and holder 51. Stop 51 engages the end of the style when it is inserted for stiffening the lead during installation and prevents the stylet from piercing the end of the lead as well as acting as a radiopaque marker for x-ray visualization during placement. The core tube 41 is bonded to the stylet stop 51 as indicated and the carbon filament strands pass around the stop 51, the stop being provided with four peripheral channels 53 as may be seen in FIG. 8.

In constructing the lead, the conductors 42, core tube 41, and stylet stop 51 are preferably assembled on a suitable mandrel. The carbon filament strands 42 are cemented to the pacer connector and then wound over the core tube 41 and past the stylet stop 51. A tubular jacket or sleeve 57 is then slipped over the body 11 of the lead. Over the entire assembly is then cast a jacket such as silicone rubber forming a shell 55 and lateral projections 59 around the tip and the jacket around the connector. After the Silastic jackets are formed, the portion of the carbon filament strands projecting beyond the stop 51 are cut off to an appropriate length. The filaments themselves having previously been bared, e.g. by burning away of the resin matrix as described earlier, so that the filaments themselves serve to establish electrical contact with the cardiac tissue. As the individual filaments are body compatible and quite compliant, the contact portion of the tip has very little force acting on it to cause fibrotic build-up.

The portion of the jacket adjacent the electrode tip is formed with two sets of lateral projections 59 which are useful in retaining the tip within the cardiac ventricle. The first set of projections next to the end stabilizes the tip with the heart movement. The second set of projections take the brunt of the forces set up by the lead movement with respect to the heart movement. The space between the projections is very flexible to prevent the transmission of the forces. The projections become enmeshed in the trabeculae at the bottom of the ventricle after the tip has been in place a few days. The projections 35 are generally flat and blade-like, but are somewhat curved in transverse section as illustrated. This curvature somewhat stiffens these projections, i.e., in the manner of a tape measure, making flexing easier when the lead is being pushed in than when it is being pulled out. The portion of the jacket over the body is preferably somewhat thinner adjacent the electrode tip portion, i.e., as indicated at 61, to provide somewhat greater compliance at this point where there is continuous flexing due to the regular beating of the heart.

As indicated previously, a lead constructed as described above is at least electrically equal to a conventional lead with a coiled metal wire, while being essentially longer-lived in terms of fatigue resistance. A further advantage of this construction struction is that it is relatively resistant to physical abuse. The entire lead is relatively flexible and the conductive elements are not liable to be damaged if the lead is crushed, e.g. by a hemostat. Likewise, the outer sheath is less likely to be cut since the inner core tube and strand winding is relatively compliant as compared with the lateral compliance of a helical metal coil. Further, although the body compatible Silastic materials may allow body salts to penetrate the lead, it is of essentially no effect since the carbon filaments are not degraded or corroded by salts as are less noble metal conductors.

The embodiment illustrated in FIG. 9 is arranged for epicardial use, and utilizes an electrode structure 65 which is adapted to be sutured to the outside of the patient's heart. Electrode structure 65 includes a flat plastic tab portion 67 which is adapted to be sutured to the patient's heart. A helical Elgiloy or platinum electrode 69 projects from one face of the tab-like portion 67 so as to imbed itself in the cardiac tissue. The body of the lead 71 is similar to the lead body illustrated in FIGS. 1-3, but the carbon filament strand 73 is connected to the epicardial form of electrode structure illustrated, rather than to the endocardial form of electrode tip.

While each of the embodiments illustrated uses but a single electrode and a single longitudinal conducting path, it should be understood that multiple conducting paths might also be provided by separating plural conductive threads with insulating material and that such multiple conductors could be used with plural stimulating electrodes, e.g. bipolar electrodes, in various arrangements known in the art.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. A lead for cardiac pacing comprising:
   at least one thread comprising a plurality of conductive carbon filaments, said thread being terminated at the distal end of said lead in an electrode structure appropriate for contacting cardiac tissue, the filaments in said thread following parallel paths from one end of said lead to the other without threads crossing one another;
   a resin matrix, a major component of which is tetrafluoroethylene, thoroughly impregnating the filaments to prevent the filaments from breaking and destructing each other during flexing of said lead;
   a terminal for connection to a cardiac stimulation pulse generator circuit, said thread being conductively connected to said terminal at the proximal end of said lead; and
   over said thread, from said electrode structure to said terminal, an insulating flexible sheath.

2. A cardiac pacer lead as set forth in claim 1 wherein said electrode structure comprised a brush-like extension of said carbon filaments extending beyond said sheath and beyond said resin matrix.

3. A cardiac pacer lead as set forth in claim 1 wherein said thread is helically formed for at least a portion of the distance between said terminal and said electrode structure.

4. A cardiac pacer lead as set forth in claim 3 wherein said terminal is hollow providing a space through which a stylet may be inserted into said helically formed thread to selectively stiffen said lead.

5. A cardiac pacer lead as set forth in claim 3 wherein said lead includes a plurality of said threads which are helically formed essentially paralleling each other at a relatively broad winding angle.

6. A cardiac pacer lead as set forth in claim 1 wherein said electrode structure comprises a metallic endocardial electrode tip.

7. A cardiac pacer lead as set forth in claim 1 wherein said electrode structure comprises an epicardial electrode including a suture pad and a metallic helical coil projecting from one face of the pad.

8. A lead for cardiac pacing comprising:
   a flexible core tube;
   at least one thread comprising a plurality of conductive carbon filaments, said thread being helically wound around said core tube with the filaments following parallel paths;
   a resin matrix, a major component of which is tetrafluoroethylene, thoroughly impregnating the filaments to prevent the filaments from breaking and destructing each other during flexing of said lead;
   an electrode structure appropriate for contacting cardiac tissue at the distal end of said lead, said thread being conductively connected to said electrode structure;
   a terminal for connection to a cardiac stimulation pulse generator circuit, said thread being conductively connected to said terminal at the proximal end of said lead; and
   over said thread and core tube, from said electrode structure to said terminal, an insulating flexible sheath.

* * * * *